United States Patent [19]

Crivello et al.

[11] Patent Number: 5,442,026
[45] Date of Patent: Aug. 15, 1995

[54] RHODIUM CONTAINING CATALYSTS FOR THE SYNTHESIS OF EPOXYSILOXANE/EPOXYSILICONE MONOMERS AND POLYMERS

[75] Inventors: James V. Crivello, Clifton Park; Mingxin Fan, Troy, both of N.Y.

[73] Assignee: General Electric Company, Waterford, N.Y.

[21] Appl. No.: 337,593

[22] Filed: Nov. 10, 1994

Related U.S. Application Data

[62] Division of Ser. No. 896,950, Jun. 11, 1992, Pat. No. 5,387,698.

[51] Int. Cl.$^6$ .............................................. C08G 77/08
[52] U.S. Cl. ...................................... 528/15; 549/215
[58] Field of Search ........................... 549/215; 528/15

[56] References Cited

U.S. PATENT DOCUMENTS

| | | | |
|---|---|---|---|
| 4,026,835 | 5/1977 | Lee et al. | 528/15 |
| 4,262,107 | 4/1981 | Eckberg | 528/15 |
| 5,169,962 | 12/1992 | Crivello et al. | 549/215 |
| 5,258,480 | 11/1993 | Eckberg et al. | 528/15 |

FOREIGN PATENT DOCUMENTS

| | | |
|---|---|---|
| A0412430 | 2/1991 | European Pat. Off. . |
| A0455257 | 11/1991 | European Pat. Off. . |
| A0476426 | 3/1992 | European Pat. Off. . |
| 1-96187 | 4/1989 | Japan . |

OTHER PUBLICATIONS

Journal of the Chemical Society, Section A.
J. L. Speier, Advances in Organometallic Chemistry, vol. 17, pp. 407–447, FGA Stone and R West, eds., Academic Press (1979).
Crivello and Lee, Journal of Polymer Science, vol. 28, pp. 479–503, John Wiley & Sons (1990).
Schweizer and Kerr, "Thermal Decomposition of Hexachloro Platinic Acid" in Inorganic Chemistry, vol. 17, pp. 2326–2327, (1978).
Lewis, Journal of the American Chemical Society, vol. 112, pp. 5998 (1990).
"Novel Platinum Containing Initiators for Ring–Opening Polymerizations", Polymer Science, Pt. A, Polymer Chem, Edition, vol. 25, pp. 1853–1863 (1991).

*Primary Examiner*—Robert E. Sellers

[57] ABSTRACT

The invention provides a method for making a curable epoxysilicone composition through the hydrosilation reaction between an ethylenically unsaturated epoxide and an SiH-containing silicone to produce an epoxysilicone product, and catalyzed by a rhodium containing selective catalyst which does not promote the oxirane ring-opening reaction of either the ethylenically unsaturated epoxide starting material or the epoxysilicone product. The rhodium containing selective catalyst has the general formula $$[R_4M]^+[RhCl_3Br]^-$$

wherein M is phosphorous or nitrogen and R is an organic radical comprising a $C_{1-18}$ linear alkyl radical, aryl, alkaryl or aralkyl radical.

2 Claims, No Drawings

RHODIUM CONTAINING CATALYSTS FOR THE SYNTHESIS OF EPOXYSILOXANE/EPOXYSILICONE MONOMERS AND POLYMERS

CROSS REFERENCE TO RELATED APPLICATIONS

This is a divisional of application Ser. No. 07/896,950 filed on Jun. 11, 1992, now U.S. Pat. No. 5,387,698.

This application is related to application Ser. No. 07/896,935, filed June 11, 1992, now abandoned; application Ser. No. 07/895,315 filed Jun. 8, 1992, now U.S. Pat. No. 5,260,399 and previously filed application Nos. 07/583,524, filed Sep. 17, 1990, now U.S. Pat. No. 5,769,962; 07/473,802, filed Feb. 2, 1990, now U.S. Pat. No. 5,128,431; and 07/802,679, filed Dec. 5, 1991, now U.S. Pat. No. 5,227,410; the entire disclosures of which are incorporated herein by reference.

BACKGROUND OF THE INVENTION

1. Field of the Invention

The invention relates to a method of producing epoxysilicones via rhodium-based catalysts which promote a hydrosilation addition reaction between an ethylenically unsaturated epoxide and an organohydrogensilane or organohydrogensiloxane, without also promoting the oxirane ring-opening polymerization of the ethylenically unsaturated epoxide starting material or the epoxysilicone hydrosilation reaction product. The invention also relates to a curable epoxysilicone composition made by the present method.

2. Technology Review

In the production of epoxysilicone compositions, transition metal catalysts have long been known to promote the hydrosilation reaction. See, for example, J.L. Speier, "Homogeneous Catalysis of Hydrosilation by Transition Metals" in *Advances in Organometallic Chemistry*, Vol. 17, pp. 407–447, F.G.A. Stone and R. West, eds., Academic Press (New York, San Francisco, London), 1979; Aylett, *Organometallic Compounds*, Vol. 1, p. 107, John Wiley & Sons (New York), 1979; and Crivello and Lee, "The Synthesis, Characterization, and Photo initiated Cationic Polymerization of Silicon-Containing Epoxy Resins" *J. Polymer Sci.*, Vol 28, pp 479–503, John Wiley & Sons (New York), 1990. Generally, the hydrosilation catalysts used are complexes of platinum, palladium, rhodium, iridium, iron or cobalt. In particular, platinum-containing catalysts have been widely used for this purpose.

The most commonly used platinum-containing hydrosilation catalysts are those derived from chloroplatinic acid. These catalysts tend to be unstable and to form metal cluster compounds or colloids (Cotton and Wilkenson, in *Advanced Inorganic Chemistry*, 4th edit., John Wiley and Sons (New York), 1980). Chloroplatinic acid itself is both thermally and photochemically unstable in solution. In addition, its composition is variable depending on its state of hydration. For example, chloroplatinic acid typically contains the $H_3O^+$, $H_5O_2^+$, and $H_7O_3^+$ ions. On standing in solution at room temperature, chloroplatinic acid will oftentimes deposit elemental platinum. On thermal decomposition, volatile $Pt_6Cl_{12}$ is also formed as one of the intermediates (Schweizer and Kerr, "Thermal Decomposition of Hexachloroplatinic Acid" in *Inorganic Chemistry*, vol. 17, pp. 2326–2327, 1978).

It has been found that in addition to catalyzing the hydrosilation reaction, many transition-metalcomplex catalysts in the presence of silicon hydrides also promote the oxirane ring-opening polymerization of the ethylenically unsaturated epoxide starting material and the epoxysilicone product of the hydrosilation reaction. Reference is made, for example, to copending, commonly assigned Application Ser. No. 07/473,802 (Riding, et al.), filed Feb. 2, 1990, now U.S. Pat. No. 5,128,431, which discloses the use of platinum or platinum-based catalysts to promote the oxirane ring-opening polymerization of epoxides. This ring-opening polymerization reaction during production of an epoxysilicone is undesirable as the epoxide polymerization may cause the reaction mixture to gel completely, resulting in the loss of the entire batch and in loss of considerable time in cleanup of the insoluble gelled resin.

Additionally, a partial gelation due to the ring-opening polymerization reaction can occur during epoxysilicone synthesis such that reproducible batch-to-batch viscosity of the epoxysilicone product is difficult to obtain. Such reproducibility in viscosity is highly preferred in the epoxysilicone industry, as these materials are typically used as coatings, for example release coatings, and the process of successfully and uniformly applying these coatings to a substrate is highly dependent upon the viscosity of the coating material. Commonly assigned, copending application Ser. Nos. 07/803,679 (now U.S. Pat. No. 5,227,420 and 07/802,681 (now U.S. Pat. No. 5,240,971, Eckberg, et al., both filed Dec. 5, 1991, disclose that viscosity control can be achieved by use of a tertiary amine stabilizer during the hydrosilation synthesis reaction. However, only a limited number of transition-metal hydrosilation catalysts are active in the presence of this stabilizer.

In the presence of precious metal hydrosilation catalysts, epoxysilicones have been found to slowly gel on storage at room temperature due to the epoxide ring-opening polymerization reaction, thus shortening the shelf-life of the epoxysilicone product. While this storage problem can be partially alleviated by deactivating the transition-metal-complex catalyst with an inhibitor of its catalytic activity, such as dodecyl mercaptan or 2-mercaptobenzothiazole in the case of platinum complexes, it would be preferable to not incorporate this extra component and additional process step into epoxysilicone composition and production process.

In most of the catalytic systems involving platinum complexes, the catalytic species is not well understood. Recently, colloids have been shown to be the active species involved in some of catalytic hydrosilation reactions (Lewis, *Journal of the American Chemical Society*, vol. 112, p. 5998, 1990) and in the ring-opening polymerization of epoxides ("Novel Platinum Containing Initiators for Ring-Opening Polymerizations", *Journal of Polymer Science*, Pt. A; Polymer Chemistry Edition, Vol. 25, 1853–1863, 1991.) Other reports suggest that the catalytic species in the hydrosilation reaction is a non-colloidal metal complex (See, for example, Harrod and Chalk, in *Organic Synthesis Via Metal Carbonyls*, p.673, Wender and Pino, eds., John Wiley & Sons (New York), 1977).

In order to minimize the oxirane ring-opening polymerization reaction, epoxysilicone fluids have been previously successfully produced only by careful control of batch temperature and olefin epoxide feed rate during the synthesis, followed by the above-mentioned inactivation of the catalyst after the completion of the hydrosilation reaction.

As disclosed in commonly assigned U.S. Patent application of Crivello and Fan, entitled "Preparation of Epoxysilicon Compounds using Rhodium Catalysts", U.S. Pat. No. 5,169,962, certain rhodium-based hydrosilation catalysts selectively promote the hydrosilation reaction without the promotion of an epoxide ring-opening polymerization reaction. A variety of epoxy-containing silicone monomers and oligomers can be synthesized using these catalysts. However, most of the catalysts traditionally used for synthesis of epoxysilicone compositions, particularly Pt-containing catalysts, promote the epoxide ring-opening polymerization reaction, and therefore do not permit the selective hydrosilation synthesis of epoxysilicones.

The use of certain quaternary onium hexachloroplatinates as catalyst for the hydrosilation reaction between phenylacetylene and triethylsilane has been previously described. Reference is made to Iovel, I., Goldberg, Y., Shymanska, M. and Lukevics, E., in *Organometallics*, vol. 6, pp. 1410–1413, 1987. However, this study did not indicate the suitability of the quaternary onium hexachloroplatinates as useful hydrosilation catalysts for addition to vinyl epoxides, nor did it suggest that such salts effectively suppress the catalyst-dependent ring-opening polymerization of epoxy groups in either the starting ethylenically unsaturated epoxide or the epoxysilicone product of the hydrosilation reaction.

In consideration of the above, it is apparent that there exists a need in the epoxysilicone industry for a method of eliminating the oxirane ring-opening when employing commonly used hydrosilation catalysts. There also exists a need for an efficient yet economical method of producing epoxysilicone monomers and oligomers in the absence of the epoxide ring-opening side reaction, thereby generating epoxysilicone compositions of reproducible batch-to-batch viscosity. There is additionally a need for epoxysilicone composition which is stable to the epoxide ring-opening reaction and, therefore, has an increased shelf-life without the additional step and cost of poisoning the catalyst after the completion of the hydrosilation addition reaction.

SUMMARY OF THE INVENTION

The present invention provides a method for making an epoxy-containing organosilicone compound, comprising the steps of:

(i) preparing the mixture comprising an ethylenically unsaturated epoxide (A), an organohydrogensilane or organohydrogensiloxane (B) and a quaternary ammonium or phosphonium rhodium halide (C); and (ii) reacting the mixture of said step (i), under conditions which promote a hydrosilation addition reaction between (A) and (B) to produce an epoxysilicone product, and which do not promote an epoxide ring-opening reaction in either (A) or in said epoxysilicone product.

The invention also provides for the novel rhodium selective catalyst (C), two methods of making the novel rhodium catalyst (C), and a curable epoxysilicone composition derived from Components (A), (B) and (C).

Thus, it is an object of the present invention to provide a method for preparing an epoxysilicone composition through the reaction between an ethylenically unsaturated epoxide and an organohydrogensilane or organohydrogensiloxane in the presence of a catalyst which efficiently promotes the hydrosilation reaction without also promoting the afore-mentioned oxirane ring-opening polymerization of either the ethylenically unsaturated epoxide starting material or the epoxysilicone product.

It is another object of the invention to provide a hydrosilation catalyst for the addition reaction between an olefin epoxide and a SiH-containing silane or siloxane to form an epoxysilicone compound, wherein the catalyst effectively promotes the hydrosilation reaction without also promoting the ring-opening polymerization of the epoxide ring in either the olefin epoxide starting material or the epoxysilicone product.

Still another object of the invention is to provide two methods of making the hydrosilation catalyst for the addition reaction between an olefin epoxide and a SiH-containing silane or siloxane to form an epoxysilicone compound, wherein the catalyst effectively promotes the hydrosilation reaction without also promoting the ring-opening polymerization of the epoxide ring in either the olefin epoxide starting material or the epoxysilicone product.

Still another object of the invention is to provide a curable epoxysilicone composition with reproducible batch-to-batch viscosity and enhanced storage life, and which is stable to oxirane ring-opening polymerization at room temperature.

DETAILED DESCRIPTION OF THE INVENTION

The present invention is based on the unexpected discovery that quaternary onium rhodium halides are effective for promoting the addition of ethylenically unsaturated epoxides to silicon hydrides without also promoting the oxirane ring-opening polymerization reaction of the epoxide starting material or the epoxysilicone final product.

Although not intending the present invention to be limited by the mechanism of operation of the quaternary salt in increasing the specificity of a rhodium halide catalyst for the hydrosilation reaction, it is believed that the onium salt stabilizes the active catalytic rhodium species, and prevents the formation of colloidal rhodium.

The present invention provides a method for making an epoxy-containing organosilicone compound, comprising the steps of:

(i) preparing the mixture comprising:

(A) from about 1 to about 20 parts by weight of the composition of an ethylenically unsaturated epoxide;

(B) from about 0.5 to about 400 parts by weight of the composition of an organohydrogensiloxane or an organohydrogensilane; based on A and (C) from about 1 to about 5000 parts per million by weight as compared to the weight of the composition of a hydrosilation catalyst of the formula

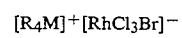

wherein M is phosphorous or nitrogen and R is an organic radical comprising $C_{1-18}$, substituted or unsubstituted, linear alkyl radical, or an aryl, alkaryl or aralkyl radical; and (ii) reacting the mixture of said step (i), under conditions which promote a hydrosilation addition reaction between (A) and (B) to produce an epoxysilicone product, and which do not promote an epoxide ring-opening reaction in either (A) or in said epoxysilicone product.

The invention also provides for the novel rhodium selective catalyst (C), two methods of making the novel rhodium catalyst (C), and a method of using the composition derived from Components (A), (B) and (C).

By not promoting the oxirane ring-opening polymerization reaction the hydrosilation catalyst (C) allows highly reactive, curable epoxysilicones with improved viscosity control and without the danger of gelation during or after synthesis. Such curable epoxysilicones are useful in the production of, for example, silicone paper release agents, decorative and protective coatings, ink, adhesives, electronics encapsulants and insulation and other uses of epoxysiloxanes.

Component (A) used in the method and composition of the present invention is an ethylenically unsaturated, i.e., either vinyl- or allyl-functional, epoxide. The ethylenically unsaturated epoxides useful in Component (A) generally include any aliphatic (glycidyl) or cycloaliphatic epoxy compounds having olefinic moieties which will readily undergo the hydrosilation addition reaction to organohydrogensilicone compounds of Component (B). Commercially available examples of such ethylenically unsaturated epoxides useful in the practice of the invention include allyl glycidyl ether; methallyl glycidyl ether; 1-methyl-4-isopropenyl cyclohexene oxide; 2,6-dimethyl-2,3 -epoxy-7-octene; 1,4 -dimethyl-4-vinylcyclohexene oxide; 4-vinylcyclohexene oxide; vinylnorbornene monoxide; dicyclopentadiene monoxide. Other suitable examples of useful ethylenically unsaturated epoxides include 1,2-epoxy-6-heptene, 1,2-epoxy-3-butene and chemically similar, unsaturated aliphatic, cycloaliphatic, and alkylaromatic epoxides.

The preferred ethylenically unsaturated epoxide is 4-vinylcyclohexene oxide.

Component (A) is used in the method and composition of the present invention in an amount ranging from about 1 to about 20 parts by weight of the composition, preferably from about 1 to about 10 parts by weight of the composition, and most preferably from about 1 to about 5 parts by weight of the composition.

Component (B) is an organohydrogensiloxane or organohydrogensilane. Suitable silicon hydride-containing starting materials generally include any silicon compound derived from a silane or at least two organosiloxane units having terminal and/or pendant SiH groups. The SiH-containing silicones useful in the practice of the invention are those capable of reacting with the ethylenically unsaturated moieties of the epoxides of Component (A) above via the hydrosilation addition reaction.

Component (B) may be either a linear hydrogen substituted polysiloxane or silane or a cyclic hydrogen substituted polysiloxane or silane, or a combination of the two. The linear hydrogen substituted polysiloxane or silane may be either branched or unbranched. In addition, Component (B) organohydrogensiloxanes useful in the invention may be copolymers, terpolymers, etc. Illustrative Examples of such copolymers are a poly(dimethyl siloxane)-poly(methylhydrogen siloxane) copolymer or, when UV cure in conjunction with onium salt catalysts is desired in the curable composition of the present invention, a polyether/hydrogensiloxane linear block copolymer, such as described in copending, commonly assigned U.S. patent application of Ser. No. 07/803,679 Eckberg, et al., now U.S. Pat. No. 5,227,410, filed Dec. 5, 1991).

Representative examples of suitable linear SiH-containing compounds include 1,1,3,3-tetraalkyldisiloxane, dialkylhydrogensiloxy-endstopped polydialkylsiloxane, copolymer comprising at least two alkylhydrogensiloxane groups, (e.g., $(CH_3)_2(H)SiO[(CH_3)_2SiO]_x[(CH_3)(H)SiO]_y\text{-}Si(H)(CH_3)_2$, where x and y are greater than or equal to 1). Other examples of SiH-containing compounds useful in the invention include 1,1,3,3-tetramethyldisiloxane, 2,4,6,8-tetramethyl-cyclotetrasiloxane methyldimethoxysilane, triethylsilane, and methyldiethoxysilane. Other examples include compounds of the formulae:

where m and n are integers and n is from about 4 to about 5000 and m is from about 3 to about 20.

The preferred linear SiH-containing silicon compound for Component (B) in the present invention is 1,1,3,3-tetramethyldisiloxane. The preferable cyclic hydride polysiloxane is 2,4,6,8-tetramethylcyclotetrasiloxane.

The preferred Component (B) in the present invention is the aforementioned 1,1,3,3-tetramethyldisiloxane.

Component (B) is used in the method and composition of the present invention in an amount ranging from about 0.5 to about 400 parts by weight of the composition, preferably from about 1 to about 200 parts by weight of the composition, and most preferably from about 1 to about 100 parts by weight of the composition based on the weight of Component (A).

Component (C) of the present invention comprises a quaternary onium rhodium halide hydrosilation catalyst of the formula

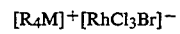

wherein M is phosphorous or nitrogen, and R is an organic radical comprising $C_{1-18}$, substituted or unsubstituted, linear alkyl, or an aryl, alkaryl or aralkyl radical.

The R substituents of Component (C) may be the same or different in any given complex and may be, for example, methyl, ethyl, n-butyl, hexyl, stearyl, phenyl, tolyl, and benzyl. By the term "substituted" it is meant an organic radical having chloro, bromo, iodo, cyano, carboxy, mercapto, hydroxy, thio, amino, nitro, phospho or other functional groups as known in the art. Moreover, heterocyclic and aromatic heterocyclic organic radicals such as pyridyl, thiophenyl, pyranyl, and the like as known in the art are also meant to be encompassed in the definition of "substituted" organic radicals. The R substituents may also represent $R^1{}_3SiQ$- groups in which Q represents a divalent aliphatic hydrocarbon radical having from 1 to 6, inclusive, carbon atoms, for example, -$CH_2$-, -$CH_2CH_2$-, and -$CH_2CHCH_3CH_2$-and each $R^1$ represents an alkyl, aryl, aralkyl, or alkaryl radical as defined and exemplified for R, above, or one $R^1$ substituent may represent a trimethylsilyl radical.

The following examples are meant to be illustrative of suitable quaternary onium rhodium halide hydrosilation catalysts useful in the practice of the invention:

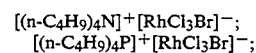

$[(n-C_{18}H_{37})_4N]^+[RhCl_3Br]^-$; and
$[(n-C_7H_{15})_4N]^+[RhCl_3Br]^-$;

The preferred hydrosilation catalyst in the practice of the invention is tetra-n-butylammonium rhodium trichloride bromide.

In addition to the high degree of selectivity of the catalysts of Component (C) described in this invention, these catalysts of Component (C) have further benefits over those previously available. For example, the catalysts are very stable and do not undergo deactivation during use in the presence of oxygen. This appears due to oxidation of the triphenylphosphine residues to triphenylphosphine oxide which does not coordinate well to the rhodium metal center. In the present catalysts, the quaternary ammonium and phosphonium ligands are not susceptable to oxidation and are, therefore, more stable under the reaction conditions. Further, the catalysts are very soluble in the reaction medium and can be used particularly in cases in which the substrate is a poor solvent with a low dielectric constant. Lastly, the catalysts of the present invention are less expensive than traditional hydrosilation catalysts such as Wilkinson's catalyst. This is because triphenylphosphine used to make this catalyst is expensive as compared to quaternary ammonium and phosphonium halides. Secondly, the new catalysts are obtained in high yields, whereas the yields of Wilkinson's catalyst are generally low and the catalyst requires extra separation and purification steps.

Component (C), the quaternary onium rhodium halide catalyst may be prepared one of two methods. One method involves producing a rhodium containing selective catalyst (C) for the synthesis of epoxysiloxane/epoxysilane monomers and polymers by first preparing a mixture of a hydrate of a rhodium halide with the general formula, $RhX_3{}^{19}mH_2O$ where X is chlorine or bromine and m is from about 1 to about 10, preferably from about 2 to about 4, and most preferably from about 3 to about 4, which is then dissolved in water; together with a quaternary onium halide dissolved in a suitable organic solvent with the general formula, $R_4M^+X^-$ where X is chlorine or bromine, and M is nitrogen or phosphorus. This mixture is then mixed. Mixing is important because it affects the reactivity of the onium salts with the rhodium salts. Mixing can be accomplished using any means that one skilled in the art would normally utilize for mixing two immiscible fluids. After mixing, the organic layer is separated from the water. The rhodium containing selective catalyst is then removed by drying or evaporation from the organic solvent. The means and methods for mixing, separating and drying or evaporation are well known in the art and are too numerous to list in this application. The following examples are used by way of illustration and not by way of limitation. An example of a means of separating the water from the organic is by using a desiccant which preferably is $CaCl_2$; and a means for evaporating or drying are respectively a rotary evaporator or by heating the mixture from about 25° to about 100° C. over a suitable period of time.

The other method of producing a rhodium containing selective catalyst (C) for the synthesis of epoxysiloxane/epoxysilane monomers and polymers is by mixing a hydrate of a rhodium halide with the general formula, $RhX_3 \cdot mH_2O$ where X is chlorine or bromine and m is from about 1 to about 10, preferably from about 2 to about 4, and most preferably from about 3 to about 4; together with a quaternary onium halide with the general formula, $R_4M^+X^-$ where X is chlorine or bromine, and M is nitrogen or phosphorus; and then mixing this combination with an organic solvent. This mixture is then mixed. Mixing is again important because it affects the reactivity of the onium salts with the rhodium salts. Mixing can be accomplished using any means that one skilled in the art would normally utilize for mixing two immiscible fluids. The solution with the rhodium containing selective catalyst can be used either directly or can be dried or evaporated and can then be used. The means and methods for mixing, and drying or evaporation are well known in the art and are too numerous to list in this application. The following examples are used by way of illustration and not by way of limitation. An example of a means of evaporating or drying are respectively a rotary evaporator or by heating the mixture from about 25° to about 100° C. over a suitable period of time.

In the method and composition of the present invention the catalysts (C) are most useful and economical in the range of from about 1 to about 5000 parts per million of the weight of the composition of pure catalyst, preferably from about 5 to about 100 parts per million of the weight of the composition, and most preferably from about 5 to about 10 parts per million of the weight of the composition, based upon the weight of the composition consisting of Components (A), (B) and (C).

To practice the method and make the curable composition of the present invention, Components (A), (B) and (C) are brought together in a reaction vessel of suitable size for the size of the batch. Addition of the Components is preferably with mixing. A volatile solvent, preferably toluene, xylene or hexane, may also be added to the reaction mixture in order to facilitate the mixing process and dispersion of the Components.

The curable epoxysilicone composition of the invention is then prepared by reacting the mixture of Components (A), (B) and (C) at a temperature in the range of from about 0° C. to about 200° C., preferably from about 25° C. to about 150° C. and most preferably from about 60° C. to about 120° C. The temperature of the reaction mixture is then maintained until the completion of the addition reaction, which can be conveniently determined through IR spectroscopy by the disappearance of the strong absorbance at 2200 cm$^{-1}$ due to the SiH group.

A preferred curable composition of the present invention comprises a (cyclohexene oxide)ethyl silane or a (cyclohexene oxide)ethyl siloxane.

In one embodiment of the invention, the present composition is readily prepared by mixing Components (A), (B), and (C) either in a reaction vessel or otherwise. In another embodiment of the invention, any two of Components (A), (B) or (C), as defined above, can be premixed, and the third Component then added later to produce the composition of the invention by the present method. Such mixtures in this embodiment exemplify the fact that the Components of the invention may be pre-mixed so as to provide what is in practicing the invention essentially a two-component system for making a curable epoxysilicone.

After the completion of the hydrosilation reaction any volatile solvent previously added can be removed from the composition of the invention through evaporation, preferably at elevated temperature and reduced pressure.

The temperature at which the composition devolitilizes (i.e., where the solvent is driven off) may be between from about 0° C. to about 200° C., preferably between from about 25° C. and about 150° C. and most preferably between from about 60° C. to about 120° C. If a tertiary amine stabilizer is incorporated into the practice of the present invention, then the temperature of devolitization may be between from about 0° C. to about 150° C., preferably between about 25° C. and about 120° C., and most preferably between from about 50° C. and 100° C.

The pressure of the stripping step is generally preferred to be below atmospheric, as such reduced pressure aids in the release of volatile molecules from the composition of the invention. Preferably the stripping step is at less than 25 torr and most preferably at less than 10 torr.

The stripping of volatile molecules, including unreacted volatile Components and low molecular weight side products of the hydrosilation reaction, may be conveniently achieved through use of a rotary evaporator, thin film evaporator, wiped film evaporator or the like.

The curable composition of the invention can be applied to cellulosic and other substrates including paper, metal, foil, polyethylene-coated paper (PEK), supercalendered paper, polyethylene films, polypropylene films and polyester films. In general, coatings can be applied to these substrates at the desired thickness. For example, the composition of the invention is readily applicable by doctor blade. For applications as a release coating, the composition of the invention is applied at a thickness of between about 0.1 mil and about 10 mils; it is also convenient to refer to such coatings in terms of coat weights, typically about 1 g/m$^2$.

The application and dispersion of the curable composition of the invention onto a substrate may be facilitated if the composition is added as a solution or dispersion in a volatile liquid carrier in which the epoxysilicone composition is soluble. When the curable composition is a polydimethylsiloxane, preferable volatile liquid carriers include, for example, hexane, xylene or toluene. It should be recognized, however, that when the curable composition of the invention is a copolymer, terpolymer, etc., the volatile solvent must be chosen such that the polymer is soluble in the solvent, which may depend upon the particular physical and chemical properties of the polymer as recognized in the art. The amount of volatile liquid carrier incorporated into the composition should not exceed about 3% by weight as compared to the total weight of the curable composition, if the advantages of using a relatively solvent-free composition are desired.

Curing of the composition of the invention can be either thermally or, in the presence of the appropriate photocatalyst and possibly cure accelerator, through UV irradiation. It has been found that the presence of the quaternary onium halorhodium complex of the composition of the invention does not substantially interfere with either of these curing methods.

Polymerization by heat involves the simple step of heating the epoxysilicones to a temperature of about 120° C. or greater, which causes the oxirane ring to open and thereby react. Reference is made in this regard to Pleudemann and Fanger, "Epoxyorganosiloxanes", *Journal of the American Chemical Society*, Vol. 81, pp. 2632–2635, 1959.

Polymerization by UV radiation involves the use of a photocatalyst that, when irradiated with UV light, forms an acid that catalyzes the crosslinking of epoxysilicone monomers through the epoxide ring-opening reaction. Such reactions are disclosed, for example, in U.S. Pat. No. 4,279,717 (Eckberg) and U.S. Pat. No. 4,617,238. Preparation of photoinitator salts useful for epoxysilicone polymerization are disclosed, for example, in Crivello and Lee, "Alkoxy-Substituted Diaryliodonium Salt Cationic Photoinitiators", *Journal of Polymer Science*, Part A: Polymer Chemistry, Vol. 27, John Wiley, New York 1989, pp. 3951–3968.

Cure performance of the composition of the invention and adhesion of the epoxysilicone product may be enhanced by the addition of epoxide monomers to the composition of the invention after the hydrosilation reaction is completed. For example, addition of up to 10 parts of an aliphatic epoxide monomer for every 10 parts epoxysilicone may result in composition exhibiting superior UV cured and anchorage on porous cellulose paper as compared to similar compositions without these "reactive diluents".

In order that persons skilled in the art may better understand the practice of the present invention, the following examples are provided by way - of illustration, and not by way of limitation. Additional information which may be useful in state-of-the-art practice may be found in each of the references and patents cited herein, which are hereby incorporated by reference.

EXAMPLES

EXAMPLE 1

Preparation of [(n-C$_4$H$_9$)$_4$N]$^+$[RhCl$_3$Br]$^-$

The following synthesis is typical of that employed for the preparation of all of the modified rhodium catalysts described in this disclosure.

Combined together were 0.05 g of rhodium trichloride hydrate dissolved in 30 mL of water and 0.10 g of tetra-n-butylammonium bromide dissolved in 20 mL methylene chloride. The mixture was stirred for 3 hours at room temperature. After this time, the purple-red methylene chloride layer was separated and dried over CaCl$_2$ for 5 hours. A red powder (the active catalyst) was obtained after removing the solvent on a rotary evaporator.

EXAMPLE 2

Preparation of [(n-C$_4$H$_9$)$_4$P]$^+$[RhCl$_3$Br]$^-$

Employing the procedure described in example 1, 0.10 g of RhCl$_3$.xH$_2$O in 100 mL water and 0.16 g of (C$_4$H$_9$)$_4$P$^+$Br$^-$ dissolved in 100 mL methylene chloride were combined. After work up as described above, the desired catalyst, [(n-C$_4$H$_9$)$_4$P]$^+$[RhCl$_3$Br]$^-$, was isolated as a light red colored powder.

EXAMPLE 3

Ring-Opening Polymerization of Cyclohexene Oxide

There were mixed together in a small vial, 1.0 g of cyclohexene oxide and 1.0 g of 1,1,3,3-tetramethyldisiloxane and 5 mg of $RhCl_3 \cdot nH_3O$. The $RhCl_3 \cdot nH_3O$ was very poorly soluble, however, after standing for one week, the reaction became visibly viscous. Analysis of the reaction mixture by gel permeation chromatography showed high molecular weight, polymeric products to be present. The experiment was repeated using $[(n-C_4H_9)_4N]^+[RhCl_3Br]^-$. Under the same conditions, no polymerization of the epoxide was observed.

EXAMPLE 4

Selective Hydrosilylations

Into a 50 mL round bottom flask equipped with a magnetic stirrer and a reflux condenser were added 2.0 g of 4-vinylcyclohexene oxide, 1.0 g of 1,1,3,3-tetramethyldisiloxane and 5 mg of $[(n-C_4H_9)_4N]^+[RhCl_3Br]$. After standing for 24 hours at room temperature, the diepoxide shown below was obtained.

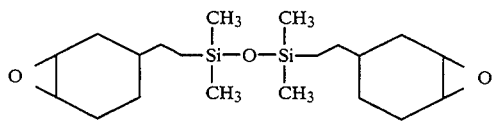

EXAMPLE 5

Example 4 was repeated replacing the catalyst with $[(n-C_4H_9)_4P]^+[RhCl_3Br]^-$. The reaction mixture was heated at 80°–90° C. for 6 hours. Again, only the diepoxide product was observed without evidence of polymer formation.

EXAMPLE 6

Example 4 was again repeated using $[(n-C_{18}H_{37})_4N]^+[RhCl_3Br]^-$ as the catalyst. In this case also, pure

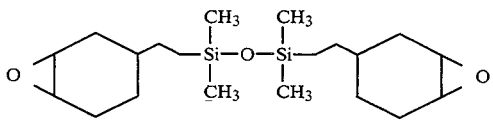

was obtained in quantitative yield without evidence of polymer formation.

EXAMPLE 7

Comparison Between Onium Salts of Rhodium, Iridium, and Ruthenium

Various onium salts $(Q^+X^-)$ were compared for the selectivity for hydrosilation over ring opening polymerization employing the following reaction.

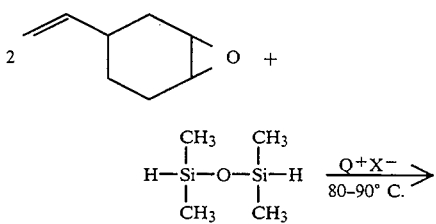

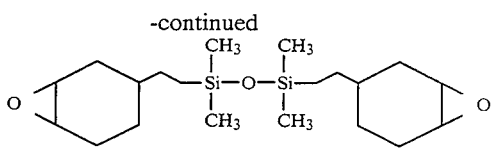

Into 1 100 mL round bottom flask were placed 2.0 g of 4-vinylcyclohexene oxide, 1.08 g of 1,1,3,3-tetramethyldisiloxane. The flask was equipped with a reflux condenser and a magnetic stirrer and the flask was placed into an oil bath heated at 80°–90° C. The results of these experiments are shown in following Table.

TABLE

| Comparison of Various Transition Metal Onium Salts. | | |
|---|---|---|
| $O^+X^-$ | Time(hr) | Results |
| $[(C_4H_9)_4N]^+[RhCl_3Br]^-$ | 1 | only diepoxide (quantitative conversion) |
| $[(C_4H_9)_4N]^+[IrCl_3Br]^-$ | 9 | Crosslinked polymer |
| $[(C_6H_5)_4As]^+[RhCl_4]^-$ | 1.5 | Crosslinked polymer |
| $[(C_4H_9)_4N]^+[RuCl_3Br]^-$ | 9 | Trace diepoxide |
| $[(C_4H_9)_4N]^+[RuCl_3Br]^-$ | 20 | Mainly starting material polymer and diepoxide. |

EXAMPLE 8

A. 0.40 g of Aliquat 336 (a commercial oily product from Henkel, $MeN(C_8H_{17})_3Cl$, 0.10 g of $RhCl_3nH_2O$ were reacted together in 4.0 mL toluene under stirring at 85° C. for 3 hours. A dark brown solution was obtained and used directly as a selective hydrosilation catalyst.

B. The above catalyst was tested for selectivity. 5 Drops of the catalyst and 0.1 mL of phenylsilane were mixed with 1.0 g of cyclohexene oxide. The resulting solution was yellow, however, no reaction was observed. This result was confirmed by GPC analysis.

C. 3 Drops of the catalyst were introduced into a reaction mixture consisting of 4.0 g 4-vinylcyclohexene oxide and 2.0 g 1,1,3,3-tetramethyldisiloxane and mixed. The solution was stirred at 85° C. for 1.5 hours, resulting in the formation of selective hydrosilation product (1,3-bis [2-(3{7-oxabicyclo[4.1.0]heptyl}ethyl]-tetramethyldisiloxane) without any polymer formation. This was confirmed by NMR and GPC analyses.

EXAMPLE 9

A. There were reacted in 50 mL toluene with stirring at 85° C. for 30 hours, 0.20 g of $(n-Bu)_4NBr$, 20.0 mg of rhodium trichloride hydrate. A brown oily product was obtained at the bottom of the reaction vessel which was used as hydrosilation catalyst.

B. The procedure of 8B was followed to test the catalyst selectivity. No polymerization was observed.

C. The procedure of 8C was followed to test the catalyst hydrosilation selectivity. The selective hydrosilation product (1,3-bis[2-(3{7-oxabicyclo [4.1.0]heptyl}ethyl]-tetramethyldisiloxane) was again obtained without any polymer formation.

It is understood that various other modifications will be apparent to and can be readily; made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present inven-

What is claimed is:

1. A compound of rhodium containing selective hydrosilation catalyst of the general formula $$[R_4M]^+[RhCl_3Br]^-$$

wherein M is phosphorous or nitrogen and R is an organic radical comprising $C_{1-18}$, substituted or unsubstituted, linear alkyl radical, or an aryl, alkaryl, or aralkyl radical.

2. The compound as set forth in claim 1 wherein the said rhodium containing selective hydrosilation catalyst is selected from the group consisting of $[(n-C_4H_9)_4N]^+[RhCl_3Br]^-$; $[(n-C_4H_9)_4P]^+[RhCl_3Br]^-$; $[(n-C_{18}H_{37})_4N]^+[RhCl_3Br]^-$; and $[(n-C_7H_{15})_4N]^+[RhCl_3Br]^-$.

* * * * *